| United States Patent [19] | [11] | 4,187,379 |
|---|---|---|
| Butler | [45] | Feb. 5, 1980 |

[54] 3-ARYLOXY-2-PYRIDINECARBONITRILE 1-OXIDE COMPOUNDS

[75] Inventor: Donald E. Butler, Ann Arbor, Mich.

[73] Assignee: Warner-Lambert Company, Morris Plains, N.J.

[21] Appl. No.: 959,802

[22] Filed: Nov. 13, 1978

[51] Int. Cl.² ............................................. C07D 213/57
[52] U.S. Cl. ..................................... 546/288; 424/263
[58] Field of Search ................................ 546/286, 288

[56] References Cited

U.S. PATENT DOCUMENTS 4,091,104  5/1978  Baldwin .............................. 546/288

*Primary Examiner*—Alan L. Rotman
*Attorney, Agent, or Firm*—Stephen Raines; David B. Ehrlinger

[57] ABSTRACT

3-Aryloxy-2-pyridinecarbonitrile 1-oxide compounds, which are useful as pharmacological agents, especially as agents for the reversal of amnesia, are disclosed. The compounds can be produced by oxidizing a 3-aryloxy-2-pyridinecarbonitrile.

7 Claims, No Drawings

3-ARYLOXY-2-PYRIDINECARBONITRILE 1-OXIDE COMPOUNDS

SUMMARY AND DETAILED DESCRIPTION

The present invention relates to new 3-aryloxy-2-pyridinecarbonitrile 1-oxide compounds. More particularly, the invention relates to new compounds of the formula

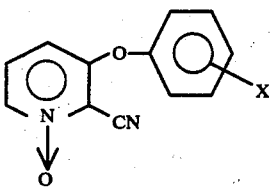

I and to a method for the production of the foregoing compounds; where X is hydrogen, chlorine or lower alkoxy and is located in the o or m positions.

The preferred compounds are those wherein X is hydrogen, chlorine, methoxy or ethoxy.

The term "lower alkoxy" is intended to mean an alkyl group of from one to four carbon atoms, such as methyl, ethyl, t-butyl, etc., linked to an oxygen atom by a single bond (methoxy, ethoxy, t-butoxy, etc.).

In accordance with the invention, the foregoing compounds of formula I can be prepared by oxidizing a compound of the formula

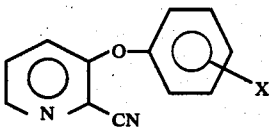

II wherein X is as previously defined.

Any oxidizing agent, such as 3 to 30% hydrogen peroxide in water, 5 to 40% peracetic acid in acetic acid, perbenzoic acid, pertrifluoroacetic acid, perphthalic acid and m-chloroperbenzoic acid may be used. Preferred is 40% peracetic acid in acetic acid. Generally an excess of oxidizing agent is employed.

The reaction may be carried out in most any organic solvent which will not undergo oxidation itself under the conditions of this reaction. This would include; glacial acetic acid, mixtures of water and acetic acid, halogenated hydrocarbons, such as dichloromethane, chloroform or tetrachloroethane. Preferred is glacial acetic acid.

The reaction is carried out at a temperature range of 0° to 100° C. for periods of from one to 24 hrs, preferably 95° to 100° C. for about 18 hrs.

The product may be isolated by distillation or crystallization.

While most of the starting materials are known compounds and the remainder are prepared by standard laboratory methods, the method of preparation of a number of starting materials of the formula II is shown in another part of the specification.

The compounds of the invention may exist in anhydrous form as well as in solvated, including hydrated forms. In general, the hydrated forms and the solvated forms with pharmaceutically-acceptable solvents are equivalent to the anhydrous or unsolvated form for the purposes of the invention.

Also in accordance with the invention, pharmaceutical compositions may be produced by formulating the compounds of formula I in dosage unit form with a pharmaceutical carrier. Some examples of dosage unit forms are tablets, capsules, lozenges, and pills; as well as powders and aqueous and non-aqueous solutions and suspensions packaged in containers containing either one or some larger number of dosage units and capable of being sub-divided into individual doses by such means as measurement into teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 1 to 500 mg, preferably 5 to 100 mg of the active ingredient per dosage unit so that the entire amount to be administered during a day can be made up from a reasonable number of dosage units.

The compounds of formula I may be incorporated into formulations intended for parenteral administration. Such compositions may be in a powdered form intended to be combined with an isotonic solution containing other ingredients such as preservatives, etc. or may be initially formulated as part of an isotonic solution which may contain preservatives, other active ingredients, etc.

The compounds of the invention are new chemical compounds of value as pharmacological agents. The compounds find use in the treatment of induced amnesia. The compounds of the invention generally would be administered to mammals in a dosage range of from about 0.014 to about 21.4 mg per kg of body weight per day, preferably 0.36 to 10.7 mg per kg per day. Thus 1 mg to 1500 mg, preferably 25 mg to 750 mg, are administered to a 70 kg host per day.

The effectiveness of the aforementioned compounds is determined by the following test. This test is designed to show the compound's ability to reverse amnesia produced by electroconvulsive shock.

One hundred male mice (Carworth, CF-1 strain, 19-21 g at time of shipment) are divided into five groups of 20 mice each. Each mouse is placed, one at a time, on a small shelf attached to the outside wall of a test box. In this position the mouse is suspended in space. Therefore, the mouse is motivated to step from the shelf through a conveniently placed small hole into the interior of the box. As soon as the mouse has all four feet within the semidarkened interior of the box, the grid floor of the box is electrified (1.5 milliamps, 3 second duration) to produce a strong pain-fear reaction from the animal. About five seconds thereafter, the mouse is removed from the test box and placed in a group holding cage.

Two hours after the above training the mice are given a single electroconvulsive shock produced by 20 milliamps delivered for 0.5 seconds through the ears. Immediately thereafter, the mice are returned to the holding cage.

Two hours after the convulsive treatment, the mice are injected intraperitoneally with the chemical being assessed. Usually three doses of the chemical will be tested at a time.

One hour after the drug treatment, the mice are tested for memory of the painful foot shock received within the self-box apparatus. This testing is accomplished by once again placing each mouse on the small shelf attached to the test box. Any mouse that stays on the shelf for 60 seconds without entering the box is counted as remembering the painful foot shock received within the box five hours earlier. Any mouse entering the box within the 60-second period is counted as having amnesia for the painful event.

Using this 60-second criterion, appropriate control experiments show (1.) 100 percent of mice will enter the box if no foot shock is delivered during the original training, (painful foot shock is necessary if the mice are to develop an aversion to entering the test box) (2.) 100 percent of mice will enter the box under the foregoing conditions even when treated with electroconvulsive shock at the three-hour point prior to testing (electroconvulsive shock treatment itself does not generate a fear of entering the test box).

The five groups of mice are treated as follows:

| Group | |
|---|---|
| (1) Ceiling Control Group: | Placebo |
| (2) Baser Line Control Group: | Electroconvulsive shock, Placebo |
| (3) 1st Drug Dose Group: | Electoconvulsive shock, 3-aryloxy-2-pyridinecarbonitrile 1-oxide compound |
| (4) 2nd Drug Dose Group: | Electroconvulsive shock, 3-aryloxy-2-pyridinecarbonitrile 1-oxide compound |
| (5) 3rd Drug Dose Group: | Electroconvulsive shock, 3-aryloxy-2-pyridinecarbonitrile 1-oxide compound |

The percentage of amnesia reversal is determined as follows for each drug group:

Percent amnesia reversal =
$$\frac{\text{Drug group} - \text{Base line control group}}{\text{Ceiling control group} - \text{Base line control group}} \times 100$$

The following criteria is used in interpreting the percent of amnesia reversal scores:
40 percent or more (active=A) 25 to 39 percent (borderline=C) and 0 to 29 percent (inactive=N). The duration of the electroconvulsive shock can be varied making the test more or less difficult for a compound to demonstrate an A or C rating. Thus a compound with activity in senile patients and in patients with early memory defects, Piracetam ® [Acta Psychiat. Scand. 54, 150 (1976)], has been administered in this test using the above methodology and 0.2 second and 0.5 second electroconvulsive shock and gave the following results.

| Piracetam ® (mg/kg) | 0.2 sec ECS | 30.5 sec ECS |
|---|---|---|
| 80 | C | N |
| 20 | A | N |
| 5 | C | N |

The inverted U shaped dose response curve is typical of this type of agent. The following table reports the results for certain compounds of the invention:

Table 1

| | LMC test | | | | | | | |
|---|---|---|---|---|---|---|---|---|
| Example # | 0.31 | 0.63 | 1.25 | 2.5 | 5.0 | 10 | 20 | 80 |
| 1 | N | A | A | A | C | N | N | |
| 2 | | | | | | A | A | N |
| 3 | | | | | | N | N | A |
| 4 | | | | | | | N | C |
| 5 | | | | | | N | | N | C |

The invention is illustrated by the following examples.

EXAMPLE 1

3-Phenoxy-2-pyridinecarbonitrile 1-oxide

A solution of 9.6 g of 3-phenoxy-2-pyridinecarbonitrile, [J. Med. Chem. 18, 1 (1975)] in 25 ml of glacial acetic acid is treated with 25 g of 40% peracetic acid in acetic acid. The mixture is heated at 95° C. for 16 hours. One hundred ml of isopropanol is added and the mixture is concentrated at reduced pressure. The residue is dissolved in 250 ml of dichloromethane and the organic layer is washed with excess dilute sodium hydroxide solution and is dried over anhydrous MgSO₄.

The drying agent is removed by filtration and the 3-phenoxy-2-pyridinecarbonitrile 1-oxide isolated by concentration at reduced pressure, mp 168°–170° C. after trituration with anhydrous diethyl ether.

EXAMPLE 2

3-(3-Methoxyphenoxy)-2-pyridinecarbonitrile 1-oxide

By substituting 6.6 g of 3-(3-methoxyphenoxy)-2-pyridinecarbonitrile for the 3-phenoxy-2-pyridinecarbonitrile in Example 1, the product is 3-(3-methoxyphenoxy)-2-pyridinecarbonitrile 1-oxide, mp 127°–128° C. after sublimation at 100° C. and 0.1 mM.

EXAMPLE 3

3-(3-Ethoxyphenoxy)-2-pyridinecarbonitrile 1-oxide

By substituting 4.8 g of 3-(3-ethoxyphenoxy)-2-pyridinecarbonitrile for the 3-phenoxy-2-pyridinecarbonitrile in Example 1, the product is 3-(3-ethoxyphenoxy)-2-pyridinecarbonitrile 1-oxide, mp 105°–107° C., after trituration with boiling anhydrous diethyl ether.

EXAMPLE 4

3-(3-Cholorphenoxy)-2-pyridinecarbonitrile 1-oxide

By substituting 5.0 g of 3-(3-chlorophenoxy)-2-pyridinecarbonitrile, [J. Med. Chem. 18, 1 (1975)] for the 3-phenoxy-2-pyridinecarbonitrile in Example 1, the product is 3-(3-chlorophenoxy)-2-pyridinecarbonitrile 1-oxide, mp 139°–141° C., after recrystallization from methanol-anhydrous diethyl ether.

EXAMPLE 5

3-(2-Chlorophenoxy)-2-pyridinecarbonitrile 1-oxide

By substituting 5 g of 3-(2-chlorophenoxy)-2-pyridinecarbonitrile for the 3-phenoxy-2-pyridinecarbonitrile in Example 1, the product is 3-(2-chlorophenoxy)-2-pyridinecarbonitrile 1-oxide, mp 156°–158° C. after recrystallization from a mixture of isopropanol, methanol and anhydrous diethyl ether.

EXAMPLE 6

Pharmaceutical Composition containing 3-Phenoxy-2-pyridinecarbonitrile 1-oxide

| Ingredient | Quantity |
| --- | --- |
| 3-Phenoxy-2-pyridinecarbonitrile 1-oxide | 150g |
| Lactose | 1038g |
| CornStarch | 39g |
| Hydroxypropyl cellulose | 30g |
| Magnesium stearate | 7g |
| Ethanol-water 50:50 | qs |

The 3-phenoxy-2-pyridinecarbonitrile 1-oxide, lactose and hydroxypropyl cellulose are blended and granulated with 50:50 ethanol water. The wet granulation is screened, dried and rescreened. The resulting dried granulation is blended with the magnesium stearate and the corn starch, and the mixture is compressed into 225 mg tablets using 11/32 inch standard concave punches. Yield equals approximately 6,000 tablets each containing 25 mg of 3-phenoxy-2-pyridinecarbonitrile 1-oxide.

Intermediates for Example 2

3-(3-Methoxyphenoxy)-2-pyridinecarbonitrile

A melt of 63 g of 3-(3-methoxyphenoxy)pyridine N-oxide is held at 95° C. and 40 g of dimethyl sulfate is added dropwise. The mixture is stirred at 105° C. for 4 hours to yield 1-methoxy-3-(3-methoxyphenoxy)-pyridinium methosulfate. This is dissolved in 100 ml water and is added dropwise to a solution of 100 g of sodium cyanide in 200 ml water held at 0°–5° C. with stirring under a nitrogen atmosphere. The mixture is stirred 18 hours and is extracted with 500 ml of chloroform. The chloroform solution is dried, concentrated and distilled to yield 3-(3-methoxyphenoxy)-2-pyridine carbonitrile, bp 125°–130° C. at 0.2 mM, mp 112°–114° C. after recrystallization from isopropanol.

3-(3-Methoxyphenoxy)pyridine 1-oxide

A solution of 68 g of 3-(3-methoxyphenoxy)pyridine in 100 ml of glacial acetic acid is treated with 75 g of 40% peracetic acid in acetic acid. The mixture is stirred 16 hours at 35° C. and then is refluxed 1 hour. The mixture is cooled, 100 ml isopropanol added, and the mixture is concentrated at reduced pressure. The oily residue is dissolved in 500 ml of dichloromethane and is washed with excess cold 25% sodium hydroxide solution. The organic layer is concentrated to yield 3-(3-methoxyphenoxy)pyridine 1-oxide, mp 75°–77° C.

3-(3-Methoxyphenoxy)pyridine

A solution of 210 g of 3-methoxyphenol in 200 ml of toluene is treated with a solution of 40 g of potassium hydroxide in 50 ml $H_2O$. The mixture is stirred and the low boiling materials distilled until the temperature reaches 180° C. One hundred g of 3-bromopyridine is added along with 0.2 g of copper bronze powder. The mixture is heated at 200° C. for 16 hours, cooled and partitioned between water and diethyl ether. The organic layer is treated with a solution of 100 g of 70% per chloric acid in 100 ml ethanol. The aqueous acid layer is separated, treated with excess 50% sodium hydroxide solution and extracted with diethyl ether. The organic layer is dried over KOH pellets, filtered, concentrated and distilled to yield 3-(3-methoxyphenoxy)pyridine, bp 163°–164° C. at 10 min.

Intermediate to Example 3

3-(3-Ethoxyphenoxy)-2-pyridinecarbonitrile

A mixture of 68 g of 3-(3-ethoxyphenoxy)pyridine 1-oxide and 40 g of dimethylsulfate is heated at 100° C. for 4 hours. The 3-(3-ethoxyphenoxy)-1-methoxy pyridinium methosulfate is dissolved in 200 ml of water and is added dropwise to a cooled, stirred solution of 75 g sodium cyamide in 200 ml of water at 0°–5° C. under a nitrogen atmosphere. The mixture is stirred 16 hours and is extracted with 500 ml of dichloromethane. The dichloromethane layer is washed with 100 ml of water, dried, concentrated and distilled to yield 3-(3-ethoxyphenoxy)-2-pyridinecarbonitrile, bp 145°–150° C. at 0.2 mM, mp 83°–84° C. after recrystallization from methanol.

3-(3-Ethoxyphenoxy)pyridine 1-oxide

A solution of 85 g of 3-(3-ethoxyphenoxy)pyridine in 500 ml of glacial acetic acid is treated with four 20 g portions of 40% peracetic acid in acetic acid. The mixture is stirred at 25° C. for 24 hours and is refluxed for 16 hours. The mixture is concentrated at reduced pressure, dissolved in 500 ml of dichloromethane and washed with excess 25% sodium hydroxide solution. The organic layer is dried, concentrated and distilled to yield 3-(3-ethoxyphenoxy)pyridine 1-oxide, bp 175°–177° C. at 0.4 mM.

3-(3-Ethoxyphenoxy)pyridine

A solution of 150 g of m-ethoxyphenol in 500 ml of toluene is treated with a solution of 56 g of potassium hydroxide in 50 ml of water. The mixture is stirred and low boiling azeotrope of water—toluene is distilled until the boiling point of pure toluene is reached. Two hundred ml of N-methyl-pyrrolidone is added and toluene is allowed to distill until the temperature of the reaction mixture reaches 165° C. Five hundred mg of copper powder is added along with 160 g of 3-bromopyridine. The mixture is refluxed for 16 hours, diluted with 500 ml of toluene, filtered and distilled to yield a mixture with bp 140°–190° C. at 10 mm. This oil is dissolved in 200 ml of isopropanol and is treated with an excess of 70% perchloric acid solution. The aqueous layer is washed with diethyl ether, made strongly basic with 50% sodium hydroxide solution and extracted with 500 ml of dichloromethane. The organic extract is dried, concentrated and distilled to yield 3-(3-ethoxyphenoxy)pyridine, bp 183°–185° C. at 10 mM.

Intermediates to Example 5

3-(2-Chlorophenoxy)-2-pyridinecarbonitrile

A mixture of 22 g of 3-(2-chlorophenoxy)pyridine 1-oxide and 22 g of dimethylsulfate is heated at 100° C. for 4 hours. The 3-(2-chlorophenoxy)-1-methoxypyridinium methosulfate is cooled and dissolved in 100 ml of water. This solution is added dropwise with stirring to a 0°–5° C. solution of 50 g of sodium cyanide in 100 ml under a nitrogen atmosphere. The mixture is stirred 16 hours and extracted with 250 ml of chloroform. The extract is dried, concentrated and distilled to yield 3-(2-chlorophenoxy)-2-pyridine-carbonitrile, bp 125°–135° C. at 01. mM, mp 90°–92° C. after recrystallization from isopropanol.

3-(2-Chlorophenoxy)pyridine 1-oxide

A solution of 74.3 g of 3-(2-chlorophenoxy)pyridine [Agr. Biol. Ghem., 34, 68 (1970)] in 75 ml of glacial acetic acid in three equal portions. The temperature is maintained at 35°–40° C. for 16 hours and 75 ml of isopropanol is added and the mixture is refluxed 1 hour. The mixture is concentrated at reduced pressure and the oil is dissolved in 500 ml of dichloromethane. The extract is washed with 25% sodium hydroxide solution, concentrated and distilled to yield 3-(2-chlorophenoxy)-pyridine 1-oxide, bp 145°–160° C. at 0.15 mM, mp 60°–64° C.

I claim:
1. A compound of the formula

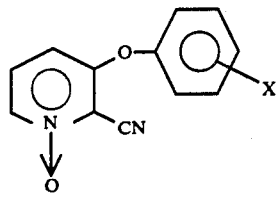

where X is hydrogen, chlorine or lower alkoxy and is in the o or m positions.
2. The compounds of claim 1 where X is hydrogen, chlorine, methoxy or ethoxy.
3. The compound of claim 1 having the name 3-Phenoxy-2-pyridinecarbonitrile 1-oxide.
4. The compound of claim 1 having the name 3-(3-Methoxyphenoxy)-2-pyridinecarbonitrile 1-oxide.
5. The compound of claim 1 having the name 3-(3-Ethoxyphenoxy)-2-pyridinecarbonitrile 1-oxide.
6. The compound of claim 1 having the name 3-(3-Chlorophenoxy)-2-pyridinecarbonitrile 1-oxide.
7. The compound of claim 1 having the name 3-(2-Chlorophenoxy)-2-pyridinecarbonitrile 1-oxide.

* * * * *